United States Patent
Nguyen et al.

(10) Patent No.: US 7,749,770 B2
(45) Date of Patent: Jul. 6, 2010

(54) MECHANICAL DEVICE FOR MIXING A FLUID SAMPLE WITH A TREATMENT SOLUTION

(75) Inventors: Hoa Nguyen, San Jose, CA (US); Urs A. Ramel, Sunnyvale, CA (US); Jeffrey A. Pierce, Redwood City, CA (US)

(73) Assignee: Bayer HealthCare LLC, Tarrytown, NY (US)

( * ) Notice: Subject to any disclaimer, the term of this patent is extended or adjusted under 35 U.S.C. 154(b) by 0 days.

(21) Appl. No.: 12/462,810

(22) Filed: Aug. 10, 2009

(65) Prior Publication Data

US 2010/0041164 A1      Feb. 18, 2010

Related U.S. Application Data

(63) Continuation of application No. 11/043,510, filed on Jan. 25, 2005, now Pat. No. 7,588,724.

(60) Provisional application No. 60/550,410, filed on Mar. 5, 2004.

(51) Int. Cl.
*G01N 1/10* (2006.01)
*G01N 33/48* (2006.01)

(52) U.S. Cl. ......................... 436/179; 422/63
(58) Field of Classification Search ................. 436/179; 422/63
See application file for complete search history.

(56) References Cited

U.S. PATENT DOCUMENTS

| | | |
|---|---|---|
| 4,024,857 A | 5/1977 | Blecher et al. |
| 4,713,974 A | 12/1987 | Stone |
| 4,935,010 A | 6/1990 | Cox et al. |
| 5,061,632 A | 10/1991 | Shepherd et al. |
| 5,208,163 A | 5/1993 | Charlton et al. |
| 5,580,794 A | 12/1996 | Allen |
| 5,837,546 A | 11/1998 | Allen et al. |
| 5,885,527 A | 3/1999 | Buechler |
| 5,912,134 A | 6/1999 | Shartle |
| 5,935,864 A | 8/1999 | Schramm et al. |
| 5,945,345 A | 8/1999 | Blatt et al. |
| 6,084,660 A | 7/2000 | Shartle |

(Continued)

FOREIGN PATENT DOCUMENTS

EP          1486766          12/2004

(Continued)

*Primary Examiner*—Jill Warden
*Assistant Examiner*—Timothy G Kingan
(74) *Attorney, Agent, or Firm*—Lerner, David, Littenberg, Krumholz & Mentlik, LLP

(57) ABSTRACT

A method of preparing a fluid sample for use in a fluid analyte monitor, the method including drawing a fluid sample into a capillary channel in a body having a septum piercing projection; piercing a first septum covering a treatment solution chamber with the septum piercing projection, thereby exposing the fluid sample in the capillary channel to the contents of the treatment solution chamber; mixing the fluid sample with the contents of the treatment solution chamber; and piercing a second septum covering the treatment solution channel such that the mixed fluid and treatment solution chamber contents are received into a fluid analyte meter. The method may also include shaking the treatment solution chamber with the capillary channel therein, thereby mixing the fluid sample with the contents of the treatment solution chamber.

20 Claims, 14 Drawing Sheets

U.S. PATENT DOCUMENTS

| | | | |
|---|---|---|---|
| 6,284,113 | B1 | 9/2001 | Bjornson et al. |
| 6,296,020 | B1 | 10/2001 | McNeely et al. |
| 6,426,230 | B1 | 7/2002 | Feistel |
| 6,521,182 | B1 | 2/2003 | Shartle et al. |
| 6,540,675 | B2 | 4/2003 | Aceti et al. |
| 6,652,814 | B1 | 11/2003 | House et al. |
| 6,673,627 | B2 | 1/2004 | Tyrrell et al. |
| 6,755,949 | B1 | 6/2004 | Bhullar et al. |
| 6,767,510 | B1 | 7/2004 | Buechler |
| 6,830,936 | B2 | 12/2004 | Anderson et al. |
| 6,901,963 | B2 | 6/2005 | Kim et al. |
| 6,905,882 | B2 | 6/2005 | Buechler |
| 6,908,593 | B1 | 6/2005 | Shartle |
| 6,919,046 | B2 | 7/2005 | O'Connor et al. |
| 6,935,772 | B2 | 8/2005 | Karp et al. |
| 6,959,615 | B2 | 11/2005 | Gamble |
| 2004/0042930 | A1 | 3/2004 | Clemens et al. |
| 2004/0063217 | A1 | 4/2004 | Webster et al. |
| 2004/0069076 | A1 | 4/2004 | Gamble |
| 2004/0168728 | A1 | 9/2004 | Schober et al. |
| 2005/0014273 | A1 | 1/2005 | Dahm et al. |
| 2005/0196872 | A1 | 9/2005 | Nguyen et al. |

FOREIGN PATENT DOCUMENTS

| | | |
|---|---|---|
| WO | WO-03044488 | 5/2003 |

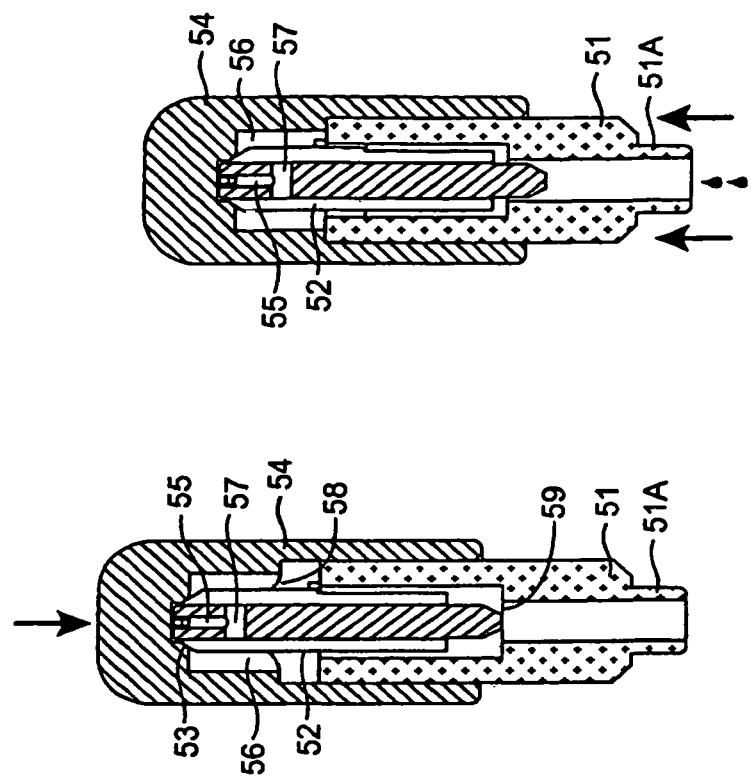
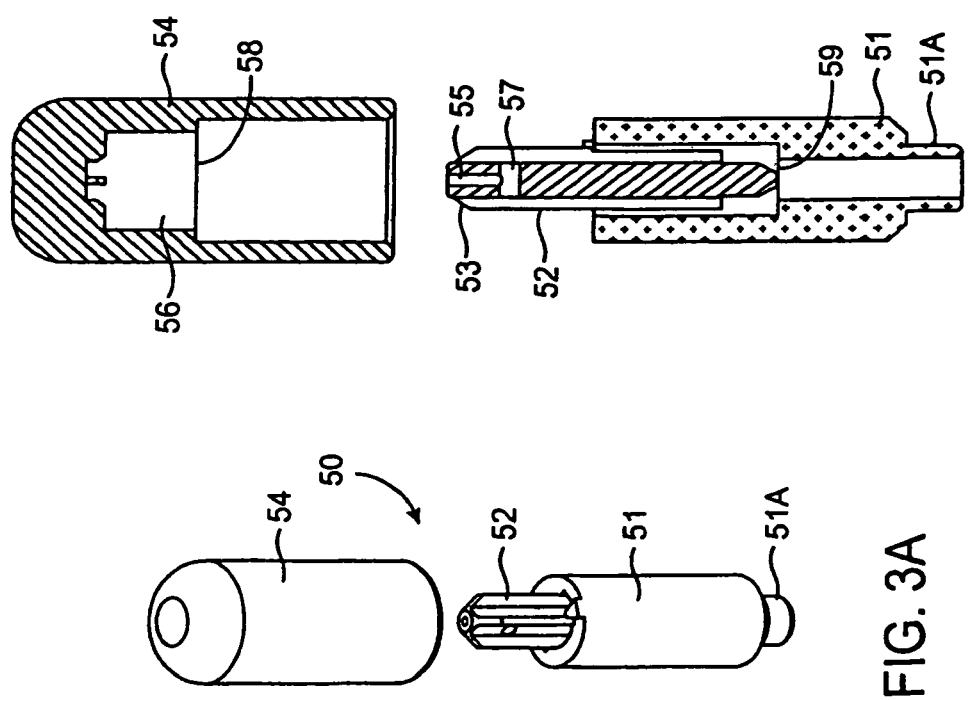

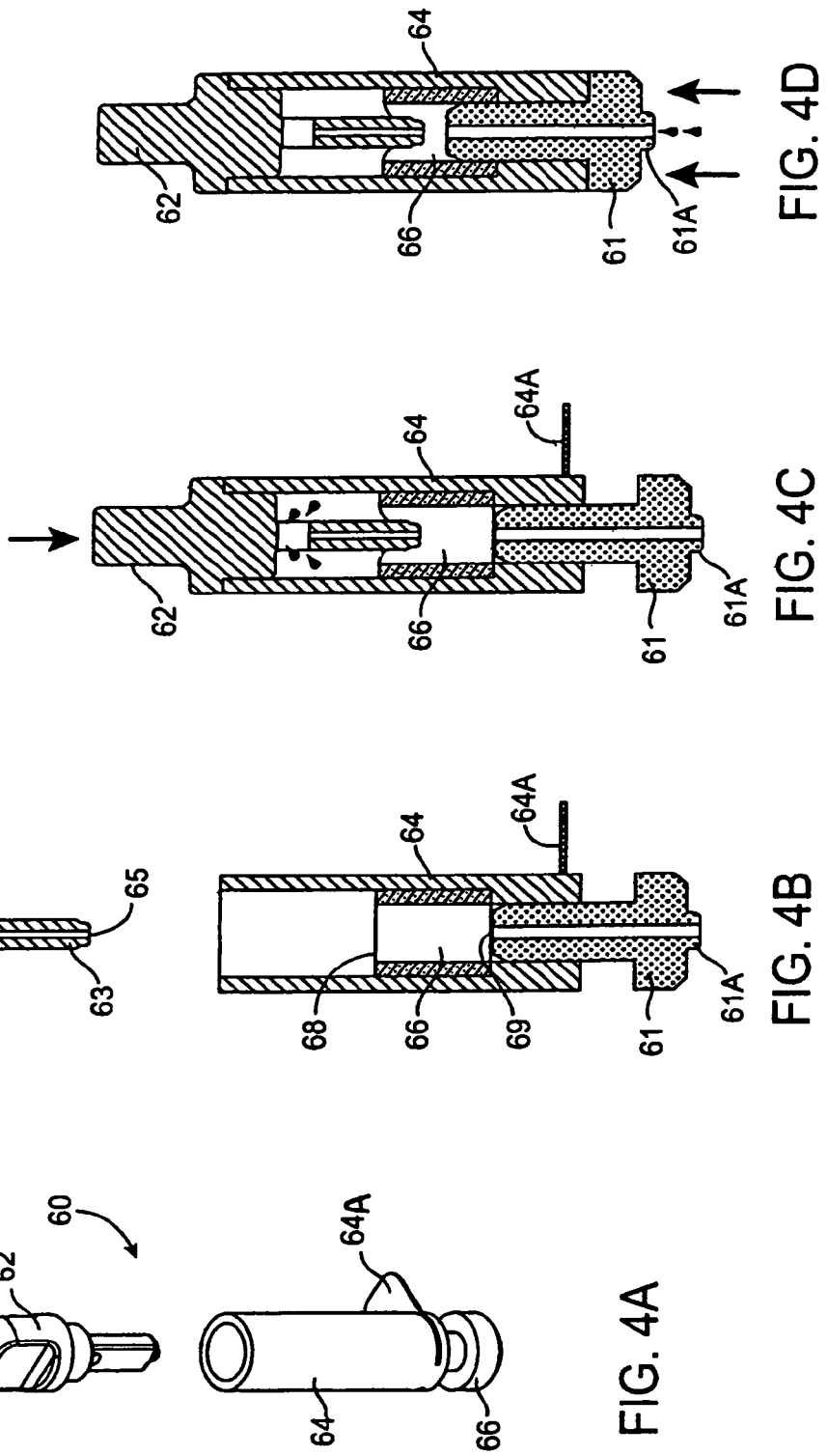

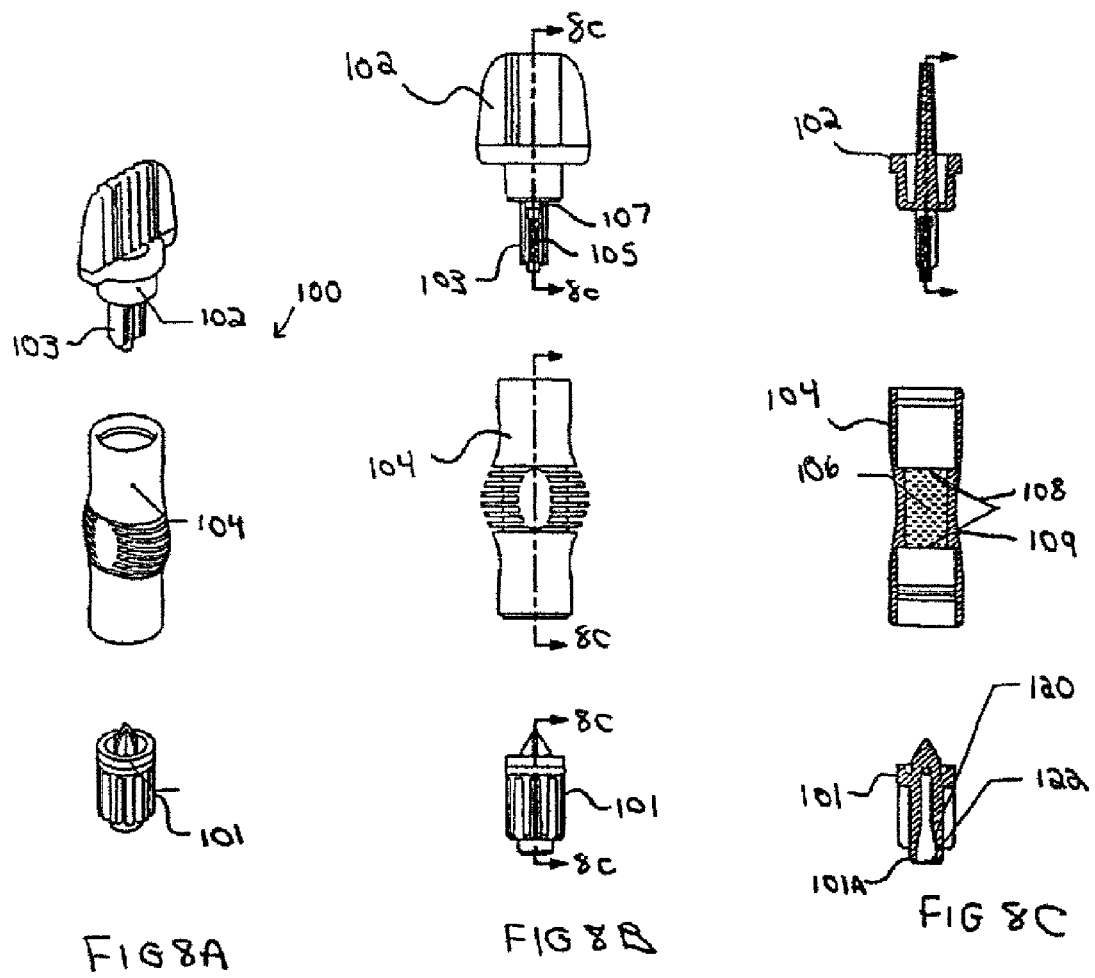

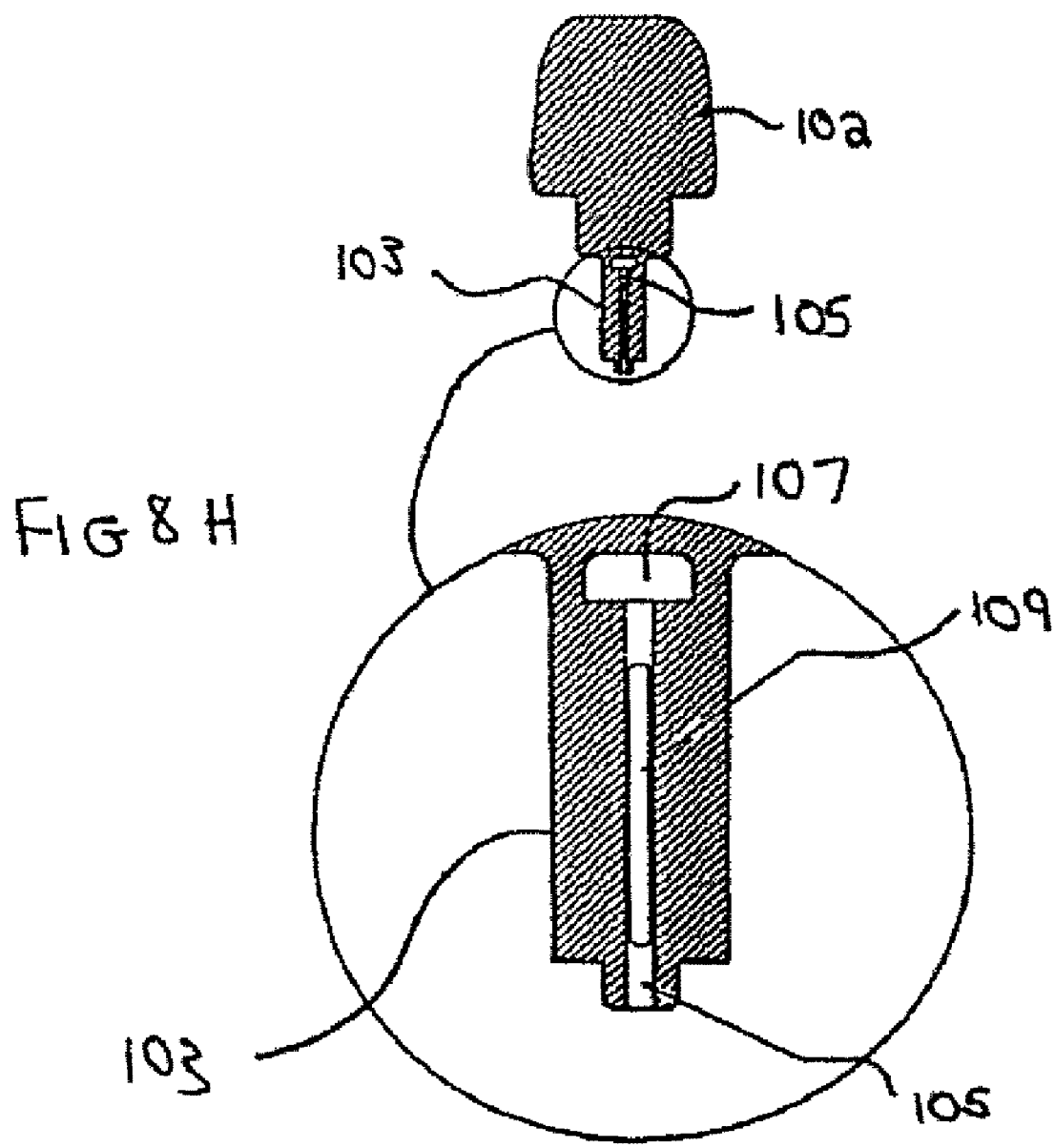

MECHANICAL DEVICE FOR MIXING A FLUID SAMPLE WITH A TREATMENT SOLUTION

CROSS REFERENCE TO RELATED APPLICATIONS

The present application is a continuation of U.S. patent application Ser. No. 11/043,510 entitled Mechanical Device For Mixing A Fluid Sample With A Treatment Solution, filed Jan. 25, 2005, which claims the benefit of the filing date U.S. Provisional Application No. 60/550,410 entitled Integrated Sampler For Use With Blood Analyte Meter, filed on Mar. 5, 2004.

TECHNICAL FIELD

The present invention is a mechanical device for mixing a fluid sample (which may optionally be a blood sample) with a treatment solution (which may optionally be a buffer or diluent).

SUMMARY OF THE INVENTION

The present invention provides an integrated system for mixing a fluid sample with a treatment solution and for delivering the mixed fluid sample and treatment solution into a meter. In preferred aspects, the fluid sample is a blood sample, the treatment solution is a buffer and the meter is a blood analyte meter, however, the present invention is not so limited. In alternate aspects, the fluid sample may be a body fluid sample including interstitial fluid or a fluid sample containing a prostate specific antigen. Moreover, although the blood analyte meter may optionally include a hemoglobin A1c (HbA1c) or lipid panel meter, the present invention is again not so limited.

In one aspect, the present invention provides a device for preparing a fluid sample for use in a meter, including: (a) a first portion, having: a septum piercing projection, and a capillary channel; and (b) a second portion, having: a treatment solution chamber, a first septum sealing the treatment solution chamber, and a second septum sealing the treatment solution chamber.

In another aspect, the present invention provides a device for preparing a fluid sample for use in a meter, including: (a) a first portion having a capillary channel dimensioned to receive a fluid sample therein; (b) a second portion having a treatment solution chamber enclosed by first and second septa, wherein the first portion penetrates the first septum when the first portion is inserted into the second portion such that contents of the treatment solution chamber mix contents of the capillary channel; and (c) a mechanism for penetrating the second septum such that contents of the treatment solution chamber and the capillary channel can be ejected from the device.

In another aspect, the present invention provides a device for preparing a fluid sample for use in a meter, including: (a) a first portion, having: a capillary channel dimensioned to receive a fluid sample therein, an internal nozzle in communication with the capillary channel, a mixing chamber in communication with both the capillary channel and the internal nozzle, and a dispensing nozzle in communication with the mixing chamber; (b) a treatment solution chamber covered by a septum; and (c) a second portion that is moveable with respect to the first portion to pierce the septum such that contents of the treatment solution chamber mix with contents of the capillary channel in the mixing chamber and are ejected through the dispensing nozzle when the second portion is moved with respect to the first portion.

In another aspect, the present invention provides a device for preparing a fluid sample for use in a meter, including: (a) a first portion having a capillary channel dimensioned to receive a fluid sample therein; (b) a treatment solution chamber enclosed by septum; and (c) a second portion, wherein the first portion penetrates the septum when the first portion is inserted into the second portion such that contents of the treatment solution chamber mix with contents of the capillary channel, such that contents of the treatment solution chamber and the capillary channel can be ejected from the device.

BRIEF DESCRIPTION OF THE DRAWINGS

FIG. 3A is a perspective view of a third embodiment of the invention prior to use.

FIG. 3B is a sectional side elevation view corresponding to FIG. 3A.

FIG. 3C is a sectional side elevation view corresponding to FIG. 3B, but with a first portion of the device being inserted into a second portion of the device, thereby penetrating a septum covering a treatment solution chamber in the second portion of the device.

FIG. 3D is a sectional side elevation view corresponding to FIG. 3C, but with a dispensing nozzle being moved with respect to the first portion of the device such that a second septum is penetrated.

FIG. 4A is a perspective view of a fourth embodiment of the invention prior to use.

FIG. 4B is a sectional side elevation view corresponding to FIG. 4A.

FIG. 4C is a sectional side elevation view corresponding to FIG. 4B, but with a first portion of the device being inserted into a second portion of the device, thereby penetrating a first septum covering a treatment solution chamber in the second portion of the device.

FIG. 4D is a sectional side elevation view corresponding to FIG. 4C, but with a dispensing nozzle being moved with respect to the first portion of the device such that a second septum is penetrated.

FIG. 8A is a perspective view of an eighth embodiment of the invention.

FIG. 8B is a side elevation view of the eighth embodiment of the invention.

FIG. 8C is sectional side elevation view corresponding to FIG. 8B.

FIG. 8H is an illustration of a system for easier washout in the first portion of the eighth embodiment of the invention.

DETAILED DESCRIPTION OF THE DRAWINGS

Figure 1A:
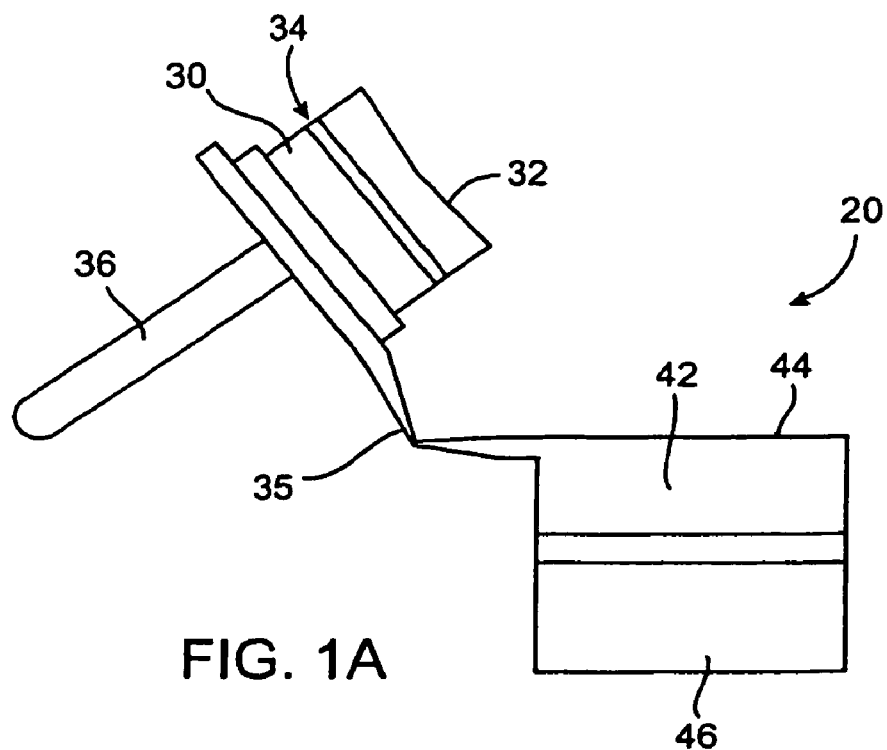
FIG. 1A is a sectional side elevation view of a first embodiment of the invention.

FIGS. 1A to 1D show a first embodiment of the invention, as follows. Device 20 includes a first portion 30 and a second portion 40. First portion 30 includes a septum piercing projection 32 and a capillary channel 34. Second portion 40 includes a treatment solution chamber 42. A first septum 44 is disposed over the top of treatment solution chamber 42, and a second septum 46 is disposed over the bottom of treatment solution chamber 42, thereby sealing the contents of treatment solution chamber 42. The first portion 30 and second portion 40 of the device may be held together by a flexible tether 35. In optional embodiments, either or both of the first and second covers 44 and 46 may be made from foil or from soft plastic film.

Figure 1B:
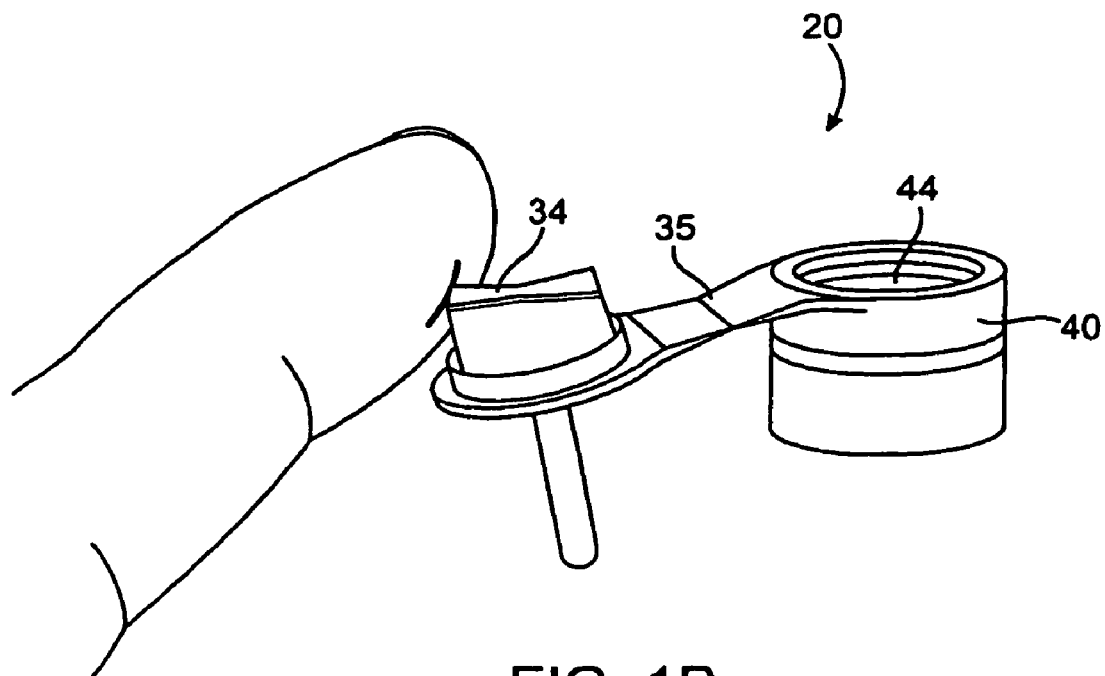
FIG. 1B is a perspective view of the first embodiment of the invention receiving a fluid sample therein.

In one preferred method of operation, a patient first uses a conventional skin lancing device to draw a drop of blood. Then, as shown in FIG. 1B, the finger is placed against the side of the body of septum piercing projection 32 such that the blood fills capillary channel 34.

It is to be understood that the present invention is not limited to use with blood samples. Instead, any other fluid that is to be analyzed in any type of fluid analysis meter may be substituted. As such, the present invention encompasses operation with various fluid samples, including body fluid samples that include analytes such as prostate specific antigen, lipids, creatinine, microalbumin, etc.

Figure 1C:
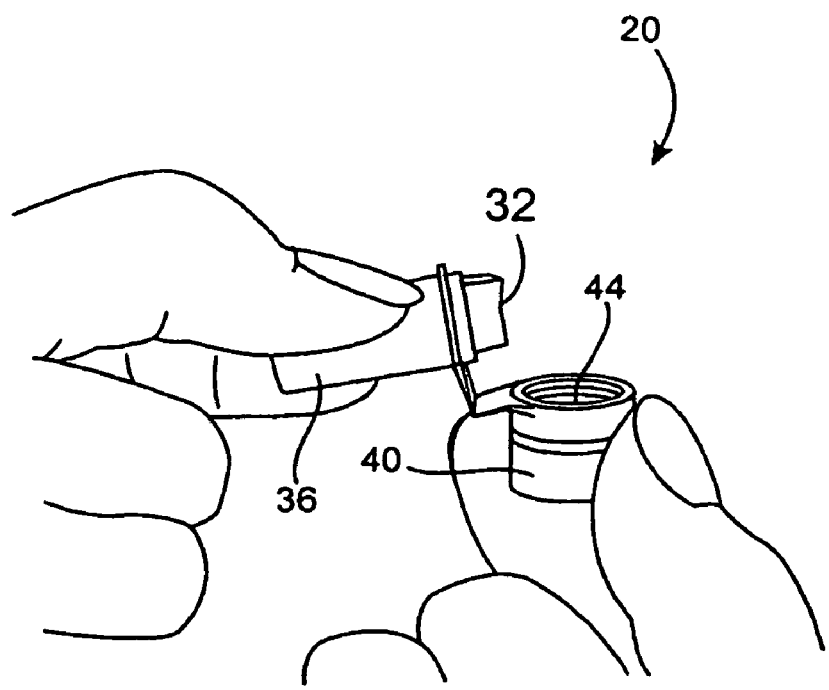
FIG. 1C is a perspective view of the first embodiment of the invention, showing a first portion of the device being inserted into a second portion of the device.

Then, as shown in FIG. 1C, the first and second portions (30 and 40) of device are mated together such that septum piercing projection 32 pierces through first septum 44, such that the blood filled capillary channel 32 is received into treatment solution chamber 42 when first portion 30 of device 20 is pushed into second portion 40 of device 20. Thus, the blood in capillary channel 32 is mixed with the contents of treatment solution chamber 42. Preferably, treatment solution chamber 42 contains a sample dilution buffer therein, but the present invention is not so limited.

Figure 1D:
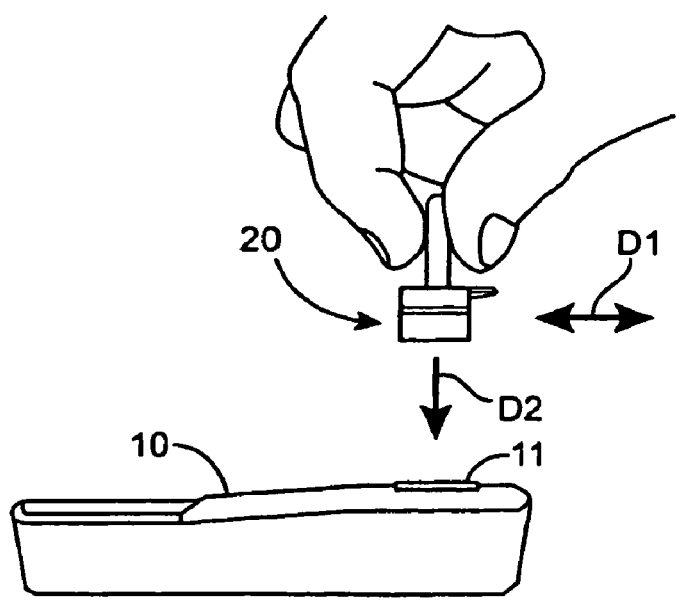
FIG. 1D is a side elevation view of the first embodiment, positioned to be shaken and then inserted into a blood analyte meter.

Then, as shown in FIG. 1D, device 20 can be shaken back and forth (in direction D1) to ensure the mixing of the contents of capillary channel 32 and treatment solution chamber 42. Then, after such mixing, device 20 can be advanced downwardly in direction D2 such that it can be inserted directly into an inlet port 11 in meter 10. When device 20 is fully inserted into meter 10, a physical component of the device penetrates septum 46. Such physical component may exist either on meter 10 or device 20, or both. When septum 46 has been penetrated, the mixed blood and treatment solution contents of treatment solution chamber 42 are then released into meter 10. In preferred embodiments, such physical component may comprise a lance or needle-type projection in meter 10 that tears into septum 46 when device 20 is received into an inlet port of meter 10. For reasons of safety, such a lance or needle-type projection can be completely disposed within meter 10. Such physical component to penetrate septum 46 may also include a mechanism that actuates to penetrate septum 46.

In alternate embodiments, the second membrane 46 covering the bottom of the treatment solution chamber 42 is not necessary. Instead, a foil seal is peeled off or a cap is removed. The contents of treatment solution chamber 42 are then simply squeezed out of the treatment solution chamber (by squeezing second portion 40 of the device), and placed directly into an inlet receiving port 11 of blood analyte meter 10.

Preferably, meter 10 is a HbA1c meter, however, it is to be understood that the present invention is not so limited. Instead, any form of analyte meter (for measuring one or more analytes) is compatible with the present invention. Thus, the present invention may entail, but is not limited to, mixing a blood sample with a dilution buffer. For example, the present invention may also be useful for mixing blood with other substances, and may also be used in conjunction with other devices. The functioning of an exemplary meter 10 was described in U.S. Pat. Nos. 5,837,546; 5,945,345 and 5,580,794, incorporated by reference herein in their entirety.

A handle 36 maybe provided opposite the septum piercing projection 32 to assist in closing device 20 (i.e. inserting first portion 30 into second portion 40). Handle 36 may also optionally assist in rotating/handling first portion 30 with respect to meter 10 (e.g.: to actuate a mechanism that penetrated septum 46).

In alternate designs of the present invention, treatment solution chamber 42 does not have a bottom septum 46 that is pierced to release the contents of treatment solution chamber 42 into meter 10. Instead, the entire second portion 40 (including treatment solution chamber 42) of the device is made of a flexible material such that the contents of treatment solution chamber 42 can simply be squeezed out (for example, through pierced septum 44, or through a spout whose cap has been removed), and dripped into meter 10.

Figure 2A:
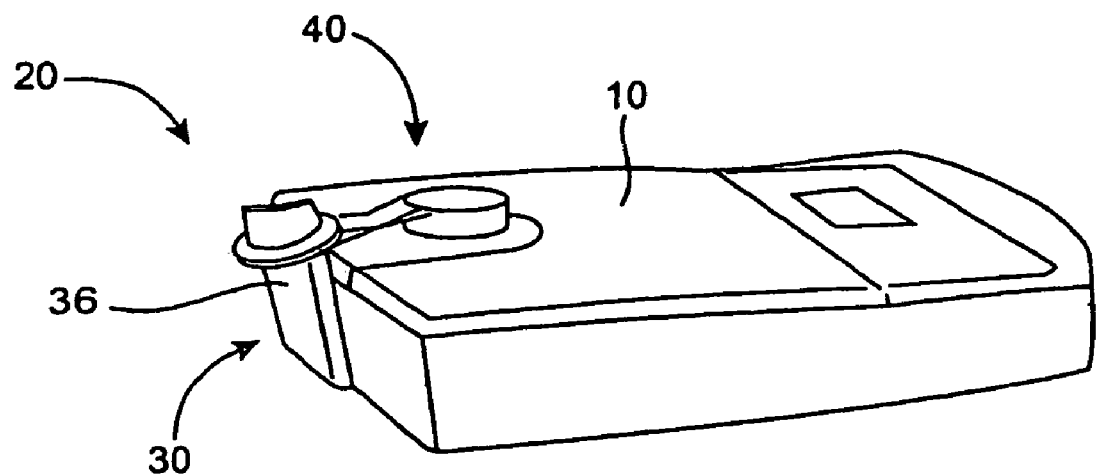
FIG. 2A is a perspective view of a second embodiment of the invention receiving a blood sample therein.
Figure 2B:
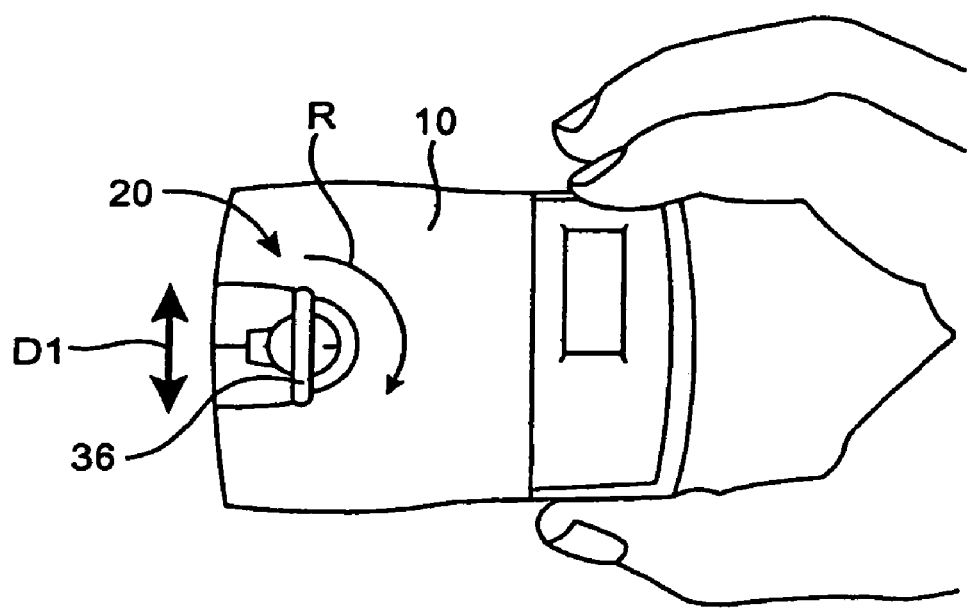
FIG. 2B is a top plan view of the second embodiment of the invention being positioned to be shaken and then rotated with respect to the blood analyte meter, so as to release a blood/buffer mixture into the analyte meter.

FIGS. 2A and 2B show a second embodiment of the invention in which device 20 is mounted directly into meter 10. This embodiment of device 20 is operated in the same manner as described above, however, the penetration of bottom septum 46 on buffer chamber 42 is instead actuated by an alternate mechanism that may simply include rotating device 20 in direction R in FIG. 2B. Prior to penetrating septum 46, however, device 20 (and meter 10 attached thereto) are preferably shaken (e.g. by rapid back and forth movement in direction D1).

A third embodiment of the invention is show in FIGS. 3A to 3D, as follows. Device 50 includes a first portion 52 having septum piercing projection 53, with a capillary channel 55 therein; and a second portion 54, including a treatment solution chamber 56, and a septum 58 sealing treatment solution chamber 56.

In one preferred method of operation, a user places a drop of blood from their finger at the top end of capillary channel 55. A stop junction 57 is provided at the opposite end of capillary channel 55. Such a stop junction may preferably comprise a bore passing through first portion 52 of device 50. Stop junction 57 thereby facilitates a predetermined volume of blood being received into capillary channel 55.

As seen in FIG. 3C, after capillary channel 55 has been filled with a blood sample, first portion 52 is then inserted into second portion 54 such that septum piercing projection 53 pierces through septum 58, such that capillary channel 55 is received into treatment solution chamber 58. Thus, the contents of capillary channel 55 and buffer chamber 56 mix together. Mixing may be further enhanced by shaking the device.

Lastly as seen in FIG. 3D, dispensing nozzle 51 is moved with respect to first portion 52 such that a second septum 59 is penetrated by first portion 52. When this occurs, the mixed blood/treatment solution is ejected from the device through dispensing nozzle 51. In preferred embodiments, distal end 51A of dispensing nozzle 51 is dimensioned to be received into a port of a blood analyte meter (that may be a HbA1c blood meter).

Also, in preferred embodiments, dispensing nozzle 51 is received into second portion 54, as illustrated. This has the advantage of trapping the blood/treatment solution mixture such that it can all be ejected through distal end 51A of dispensing nozzle 51.

First and second septums 58 and 59 may be made of foil. However, the present invention is not so limited. Septums 58 and 59 may be made of any suitable material, including plastic or rubber.

The embodiment of the invention shown in FIGS. 3A to 3D may optionally be used with the blood analyte meter (10 in FIGS. 1D and 2B) as described above. It is to be understood, however, that this embodiment of the invention may also be used with any suitable fluid analysis meter, or even with a simple containment vessel (e.g.: for preparing a sample for deposition in a well, such that it can be analyzed in future).

System 50 may also be used for preparing a blood sample for use in a blood analyte meter 10 by: drawing blood into capillary channel 55 in a body 52 having a septum piercing projection 53; piercing a first septum 58 covering a treatment solution chamber 56 with septum piercing projection 53, thereby exposing the blood in capillary channel 55 to the contents of treatment solution chamber 56; shaking treatment solution chamber 56 with capillary channel 55 received therein, thereby mixing the blood with the contents of treatment solution chamber 56; and piercing a second septum 59 such that the mixed blood and treatment solution chamber contents are received into blood analyte meter 10.

System 50 may also be used for preparing a blood sample for use in blood analyte meter 10, by: drawing a blood sample into capillary channel 55 in first portion 52 of the device; moving a second portion 54 of the device with respect to first portion 52 to penetrate septum 58 of treatment solution chamber 56 such that contents of treatment solution chamber 56 are mixed with the blood sample in capillary channel 55; and ejecting the mixed treatment solution and blood sample through dispensing nozzle 51 and into a blood analyte meter 10.

A fourth embodiment of the invention is show in FIGS. 4A to 4D, as follows. Device 60 includes a first portion 62 having septum piercing projection 63, with a capillary channel 65 therein; and a second portion 64, including a treatment solution chamber 66, and a top septum 68 sealing treatment solution chamber 66.

In one preferred method of operation, a user places a drop of blood from their finger at the top end of capillary channel 65. A stop junction 67 is provided at the opposite end of capillary channel 65. Such a stop junction may preferably comprise a bore passing through first portion 62 of device 60. Stop junction 67 thereby facilitates a predetermined volume of blood being received into capillary channel 65.

As seen in FIG. 4C, after capillary channel 65 has been filled with a blood sample, first portion 62 is then inserted into second portion 64 such that septum piercing projection 63 pierces through top septum 68, such that capillary channel 65 is received into treatment solution chamber 66. Thus, the contents of capillary channel 65 and treatment solution chamber 66 mix together. Mixing may be further enhanced by shaking the device.

Lastly as seen in FIG. 4D, removable safety tab 64A can be removed such that dispensing nozzle 61 can be moved with respect to first portion 62 such that a second (i.e.: bottom) septum 69 is penetrated by first portion 62. When this occurs, the mixed blood/treatment solution is ejected from the device through dispensing nozzle 61. In preferred embodiments, distal end 61A of dispensing nozzle 61 is dimensioned to be received into a port of a blood analyte meter (including a hemoglobin A1c blood meter).

Also, in preferred embodiments, dispensing nozzle 61 is received into first portion 64, as illustrated. This has the advantage of trapping the blood/treatment solution mixture such that it can all be ejected through dispensing nozzle 61.

First and second septums 68 and 69 may be made of foil. However, the present invention is not so limited. Septums 68 and 69 may be made of any suitable material, including plastic or rubber.

The embodiment of the invention shown in FIGS. 4A to 4D may optionally be used with the blood analyte meter (10 in FIGS. 1D and 2B) as described above. It is to be understood, however, that this embodiment of the invention may also be used with any suitable fluid analysis meter, or even with a simple containment vessel (e.g.: for preparing a sample for deposition in a well, such that it can be analyzed in future).

System 60 may also be used for preparing a blood sample for use in a blood analyte meter 10 by: drawing blood into capillary channel 65 in a body 62 having a septum piercing projection 63; piercing a first septum 68 covering treatment solution chamber 66 with septum piercing projection 63, thereby exposing the blood in capillary channel 65 to the contents of treatment solution chamber 66; shaking treatment solution chamber 66 with capillary channel 65 received therein, thereby mixing the blood with the contents of treatment solution chamber 66; and piercing a second septum 69 such that the mixed blood and treatment solution chamber contents are received into blood analyte meter 10.

System 60 may also be used for preparing a blood sample for use in blood analyte meter 10, by: drawing a blood sample into capillary channel 65 in first portion 62 of the device; moving a first portion 62 of the device with respect to second portion 64 to penetrate septum 68 of treatment solution chamber 66 such that contents of treatment solution chamber 66 are mixed with the blood sample in capillary channel 65; and ejecting the mixed treatment solution and blood sample through dispensing nozzle 66 and into a blood analyte meter 10.

A fifth embodiment of the invention is show in FIGS. 5A to 5C, as follows. Device 70 includes a first portion 72 having septum piercing projection 73, with a capillary channel 75 therein; and a second portion 74, including a treatment solution chamber 76, and a septum 78 sealing treatment solution chamber 76. First portion 72 further includes capillary channel 75, an internal nozzle 77 (comprising a narrow internal nozzle 77A and a wide buffer receiving channel 77B), a mixing chamber 79 and a dispensing nozzle 71.

In one preferred method of operation, a user places a drop of blood from their finger at the top end of capillary channel 75. As seen in FIG. 5B, after capillary channel 75 has been filled with a blood sample, first portion 72 is then inserted into second portion 74. As a result, septum piercing projection 73 pierces through septum 78, forcing the treatment solution in buffer chamber 76 to pass through treatment solution receiving channel 77A, internal nozzle 77B and into mixing chamber 79. As a result of this flow of treatment solution, the blood sample in capillary channel 75 is also drawn into mixing chamber 79. Then, the mixed contents of mixing chamber 79 are ejected through dispensing nozzle 71 when second portion 74 is moved with respect to first portion 72.

Internal nozzle 77B and capillary channel 75 preferably meet at a Y-junction adjacent to an inlet to mixing chamber 79, as illustrated. This assists the buffer solution passing through internal nozzle 77B in drawing the blood sample from capillary channel 75 into the mixing chamber.

In preferred embodiments, mixing chamber 79 further includes a protrusion 79A that assists in causing turbulent fluid mixing within mixing chamber 79.

In preferred embodiments, the distal end of dispensing nozzle 71 is dimensioned to be received into a port of a blood analyte meter (including a hemoglobin A1c blood meter).

Septum 78 maybe made of foil, or any other suitable material, including plastic or rubber.

Figure 5A:
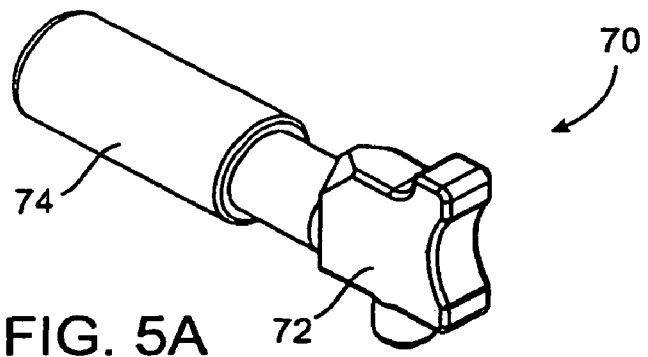
FIG. 5A is a perspective view of a fourth embodiment of the invention prior to use.
Figure 5B:
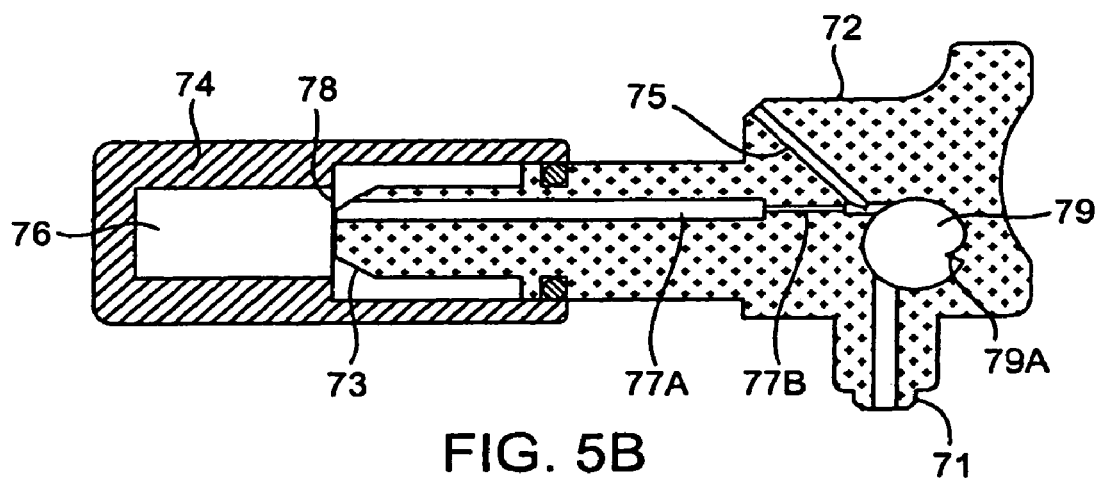
FIG. 5B is a sectional side elevation view corresponding to FIG. 5A.
Figure 5C:
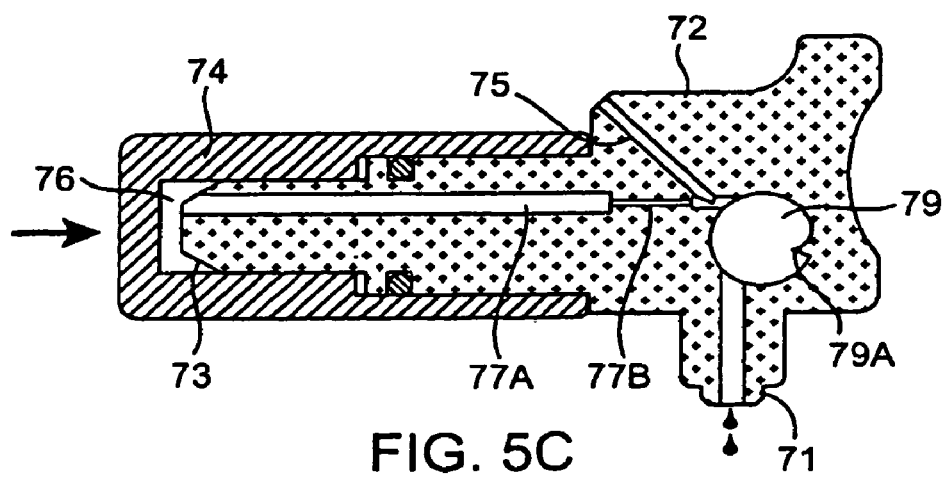
FIG. 5C is a sectional side elevation view corresponding to FIG. 5B, but with a first portion of the device being inserted into a second portion of the device, thereby penetrating a septum covering a treatment solution chamber in the second portion of the device, causing a fluid sample in the capillary channel and treatment solution in the treatment solution chamber to be mixed together and dispensed through a dispensing nozzle.

The embodiment of the invention shown in FIGS. 5A to 5C may optionally be used with the blood analyte meter (10 in FIGS. 1D and 2B) as described above. It is to be understood, however, that this embodiment of the invention may also be used with any suitable fluid analysis meter, or even with a simple containment vessel (e.g.: for preparing a sample for deposition in a well, such that it can be analyzed in future).

System 70 may also be used for preparing a blood sample for use in a blood analyte meter 10, by: drawing a blood sample into capillary channel 75 in first portion 72 of the device; moving a second portion 74 of the device with respect to first portion 72 to penetrate a septum 78 of treatment solution chamber 76 such that contents of treatment solution chamber 76 are mixed with the blood sample in capillary channel 75; and ejecting the mixed treatment solution and blood sample through dispensing nozzle 71 and into a blood analyte meter.

A sixth embodiment of the invention is show in FIGS. 6A to 6C, as follows. Device 80 includes a first portion 82 and a second portion 84. First portion 82 includes a capillary channel 85, a treatment solution chamber 86, and a septum 88 sealing treatment solution chamber 86. First portion 82 further includes an internal nozzle 87 (comprising a treatment solution receiving channel 87A and a mixing chamber 89). The distal end 81 of first portion 82 is preferably shaped as a dispensing nozzle that may be receivable into an inlet port of a blood analyte meter.

In one preferred method of operation, a user places a drop of blood from their finger at the top end of capillary channel 85. As seen in FIG. 8B, after capillary channel 85 has been filled with a blood sample, second portion 84 is then inserted into first portion 82. As a result, septum piercing projection 83 pierces through septum 88, forcing the treatment solution in treatment solution chamber 86 to pass through treatment solution receiving channel 87A, internal nozzle 87B and into mixing chamber 89. As a result of this flow of treatment solution, the blood sample in capillary channel 85 is also drawn into mixing chamber 89. Then, the mixed contents of mixing chamber 89 are ejected through dispensing nozzle 81 when second portion 84 is moved with respect to first portion 82.

Internal nozzle 87B and capillary channel 85 preferably meet at a Y-junction adjacent to an inlet to mixing chamber 89, as illustrated. This assists the treatment solution passing through internal nozzle 87 in drawing the blood sample from capillary channel 85 into mixing chamber 89.

In preferred embodiments, mixing chamber 89 comprises a twisted path with various protrusions 79A that assists in causing turbulent fluid mixing within mixing chamber 89.

In preferred embodiments, the distal end of dispensing nozzle 81 is dimensioned to be received into a port of a blood analyte meter (including a hemoglobin A1c blood meter).

Septum 88 maybe made of foil, or any other suitable material, including plastic or rubber.

Figure 6C:
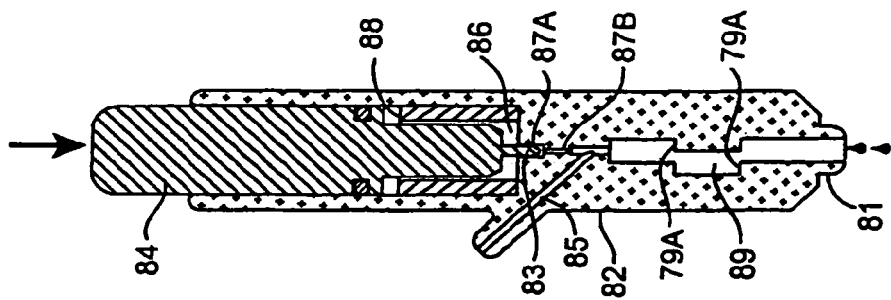
FIG. 6C is a sectional side elevation view corresponding to FIG. 6B, but with a first portion of the device being inserted into a second portion of the device, thereby penetrating a septum covering a treatment solution chamber in the second portion of the device, causing a fluid sample in the capillary channel and treatment solution in the treatment solution chamber to be mixed together and dispensed through a dispensing nozzle.
Figure 6B:
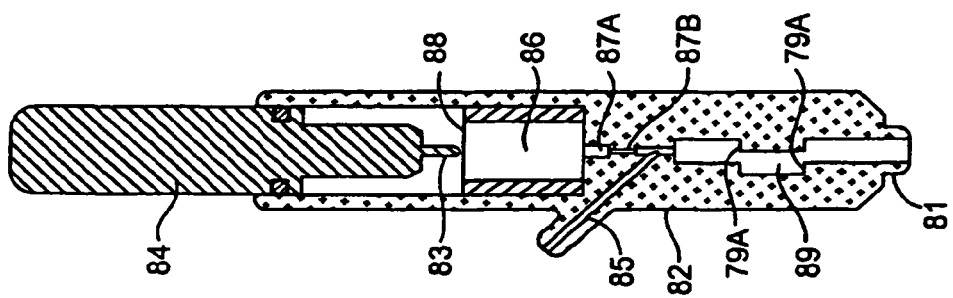
FIG. 6B is a sectional side elevation view corresponding to FIG. 6A.
Figure 6A:
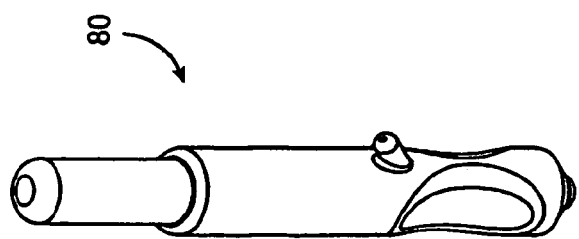
FIG. 6A is a perspective view of a fifth embodiment of the invention prior to use.

The embodiment of the invention shown in FIGS. 6A to 6C may optionally be used with the blood analyte meter (10 in FIGS. 1D and 2B) as described above. It is to be understood, however, that this embodiment of the invention may also be used with any suitable fluid analysis meter, or even with a simple containment vessel (e.g.: for preparing a sample for deposition in a well, such that it can be analyzed in future).

System 80 may also be used for preparing a blood sample for use in a blood analyte meter 10, by: drawing a blood sample into capillary channel 85 in first portion 82 of the device; moving a second portion 84 of the device with respect to first portion 82 to penetrate a septum 88 of treatment solution chamber 86 such that contents of treatment solution chamber 86 are mixed with the blood sample in capillary channel 85; and ejecting the mixed buffer and treatment solution sample through dispensing nozzle 81 and into a blood analyte meter.

In various aspects of the invention, devices 20, 50, 60, 70 and 80 maybe used with either: a single use test meter 10 (as was described in U.S. Pat. Nos. 5,837,546; 5,945,345 and 5,580,794), or a multi-use cartridge system as described in U.S. Provisional Application No. 60/550,410.

Figure 7A:
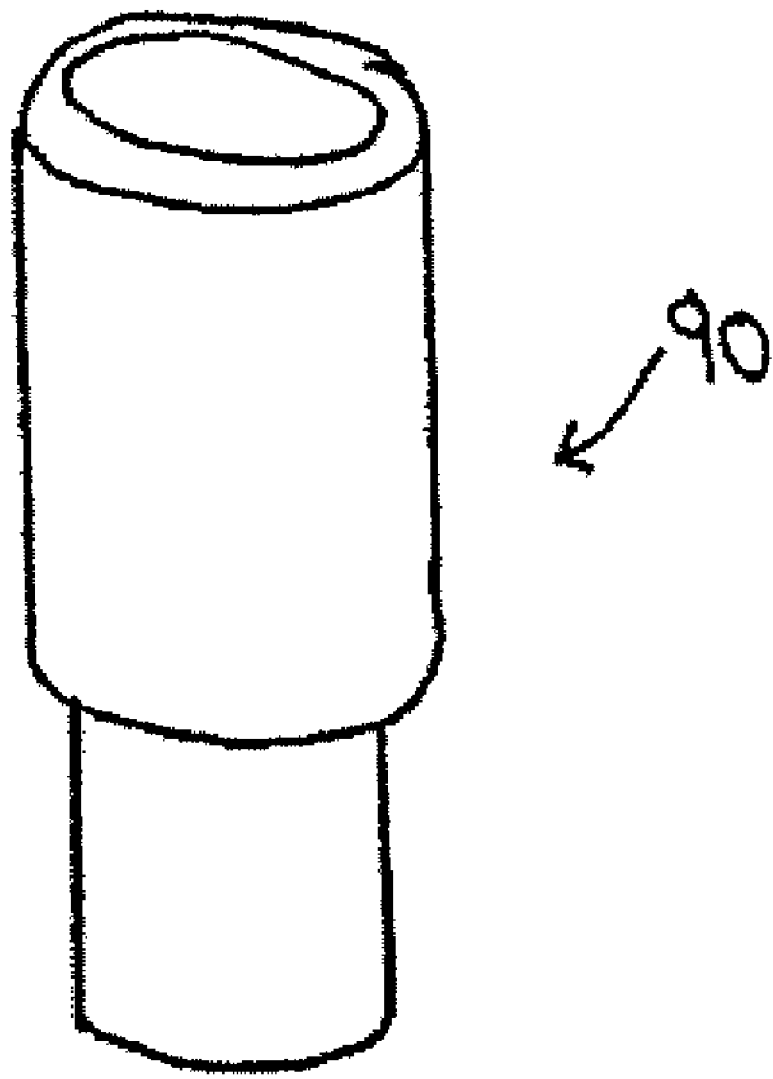
FIG. 7A is a perspective view of a sixth embodiment of the invention prior to use.
Figure 7B:
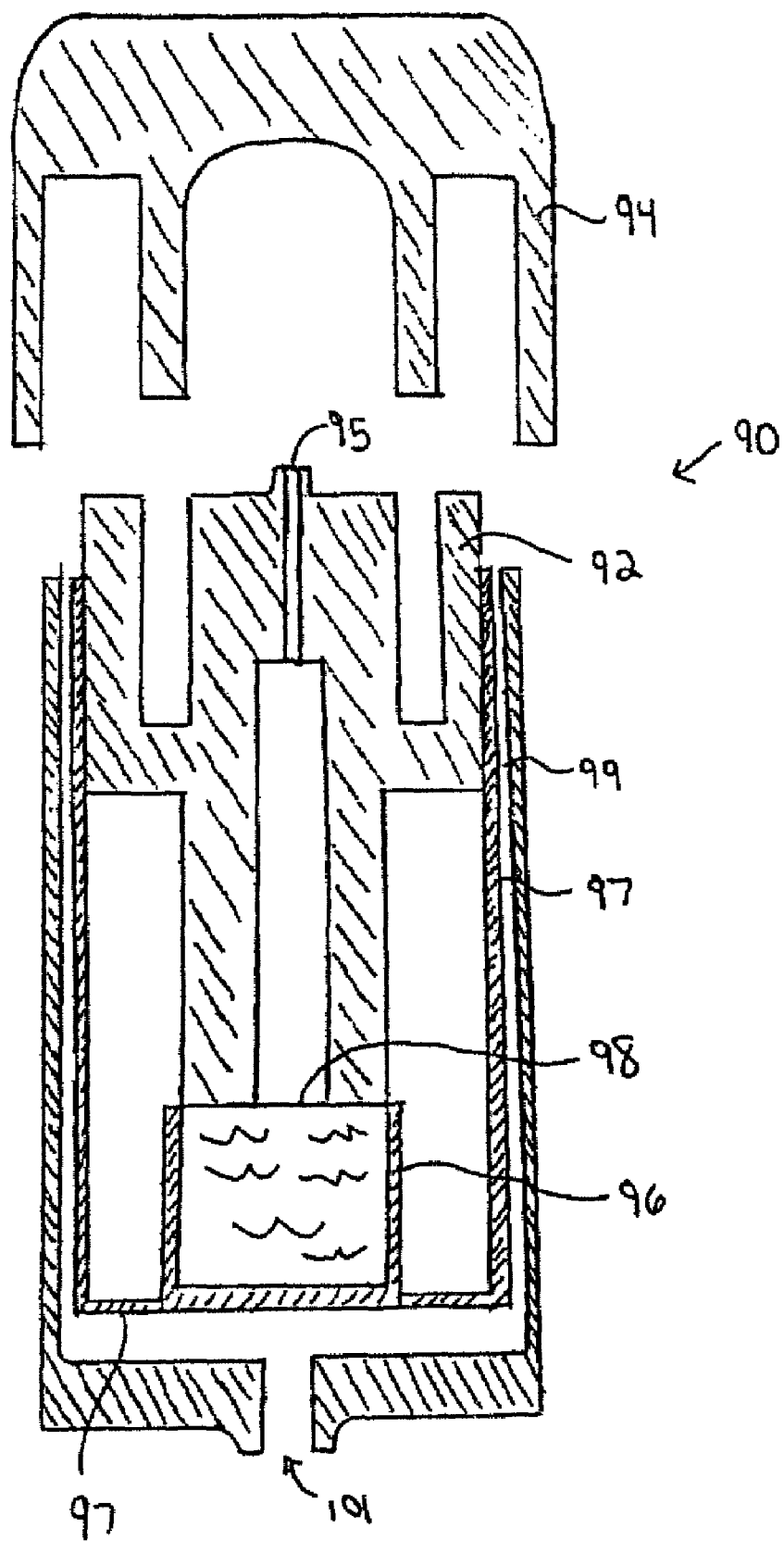
FIG. 7B is a sectional side elevation view corresponding to FIG. 7A.
Figure 7C:
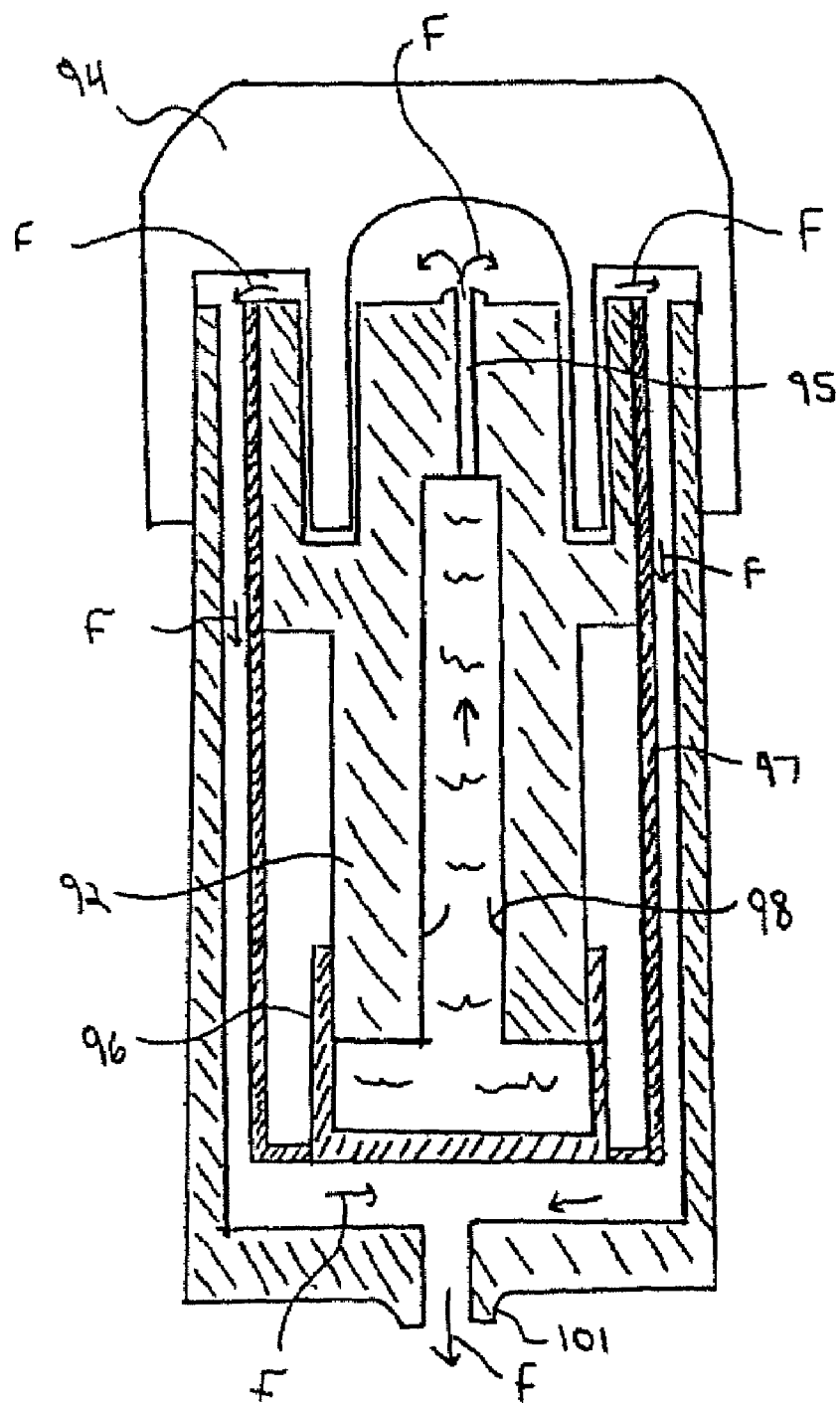
FIG. 7C is a sectional side elevation view corresponding to FIG. 7B, but with a first portion of the device being inserted into a second portion of the device, thereby causing the first portion to penetrate a septum covering a treatment solution chamber, causing a fluid sample in the capillary channel and treatment solution in the treatment solution chamber to be mixed together and dispensed through a dispensing nozzle.
Figure 7D:
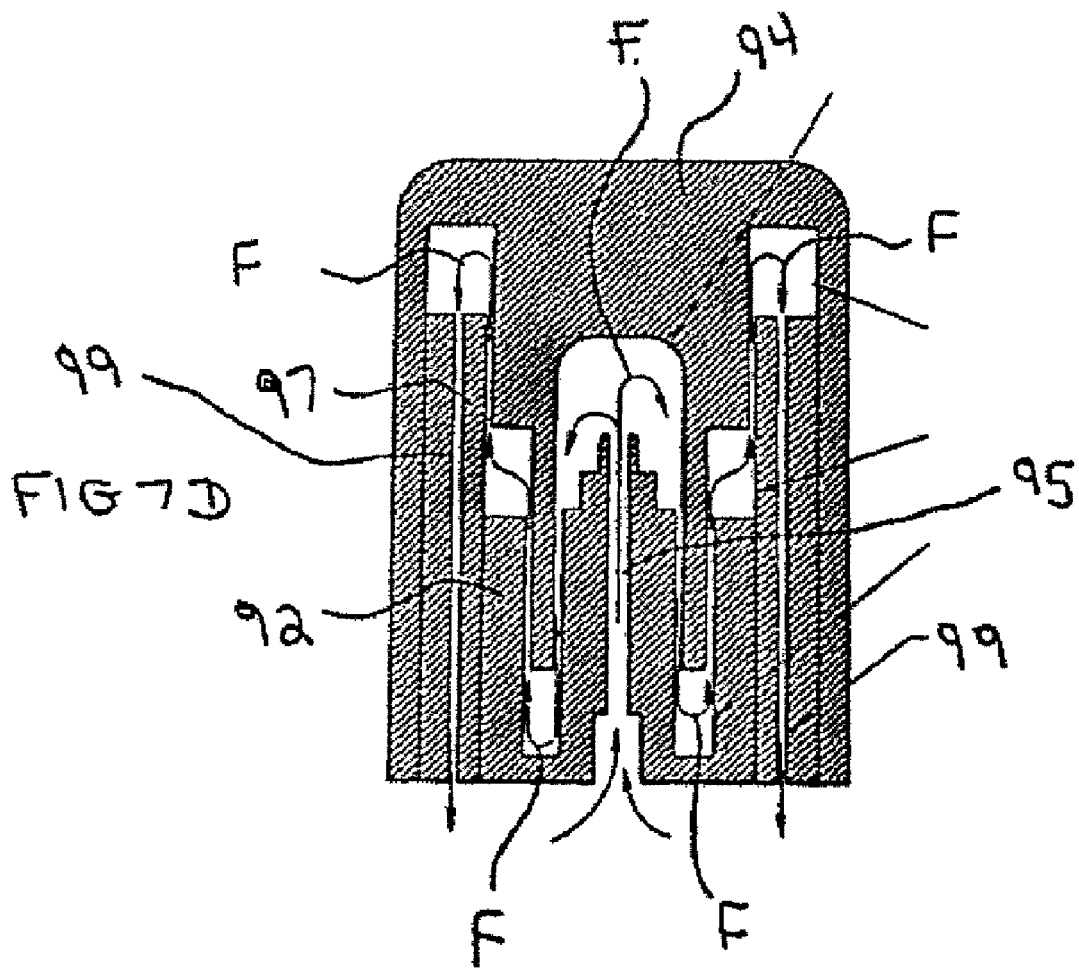
FIG. 7D is a sectional side elevation view corresponding to FIG. 7B, showing fluid flow between the first and second portions of the device when the first portion of the device is inserted into the second portion of the device.
Figure 7E:
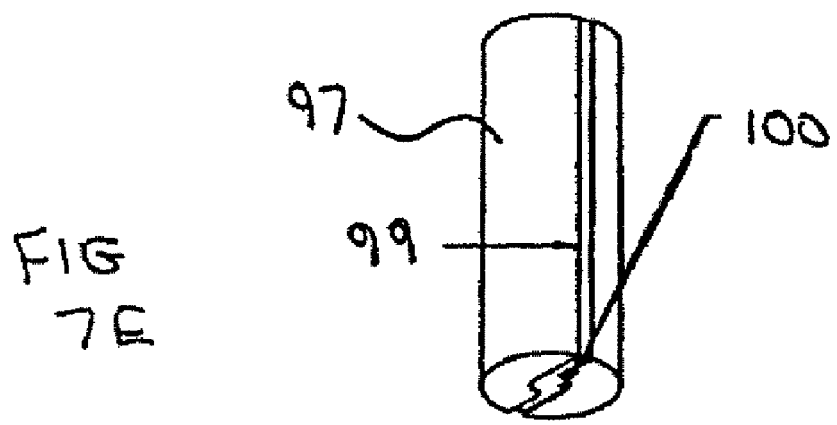
FIG. 7E is a bottom perspective view of a third portion of the device, in which the treatment solution chamber is housed, corresponding to FIG. 7B.

A seventh embodiment of the invention is shown in FIGS. 7A to 7E, as follows. Device 90 includes a first portion 92, a second portion 94, and a third portion 97. First portion 92 includes a capillary channel 95. Third portion 97 houses a treatment solution chamber 96, and a septum 98 sealing treatment solution chamber 96. A blood (or other fluid) sample is received into capillary channel 95. As shown in FIG. 7C, when first portion 92 is inserted into second portion 94, the bottom end of first portion 92 penetrates septum 98 and the contents of treatment solution chamber 96 are pushed upwardly through capillary channel 95. Thus, the contents of treatment solution chamber 96 are mixed with the contents of capillary channel 95. This mixing fluid flow is shown by arrows F in FIGS. 7C and 7D. FIG. 7E shows a bottom perspective view of third portion 97, showing side flues 99 and bottom groove 100, which further enhances mixing prior to fluid ejection through distal end 101 of the device. Distal end 101 of device 90 is preferably shaped as a dispensing nozzle that may be receivable into an inlet port of a blood analyte meter.

An eighth embodiment of the invention is shown in FIGS. 8A to 8G, (operating similar to the fourth embodiment of the invention shown in FIGS. 4A to 4D), as follows. Device 100 includes a first portion 102 having a septum piercing portion 103 with a capillary channel 105 therein; and a second portion 104, including a treatment solution chamber 106, and a top septum 108 sealing treatment solution chamber 106.

In one preferred method of operation, a user places a drop of blood from their finger at the top end of capillary channel 105. A stop junction 107 is provided at the opposite end of capillary channel 105. Such a stop junction may preferably comprise a bore passing through first portion 102 of device 100. Stop junction 107 thereby facilitates a predetermined volume of blood being received into capillary channel 105.

Figure 8D:
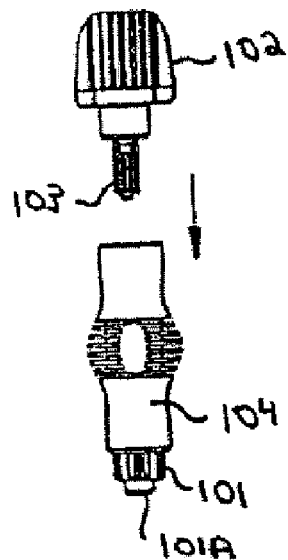
FIG. 8D is aside elevation view of the first portion of the eighth embodiment of the device being inserted into the second portion of the device.
Figure 8E:
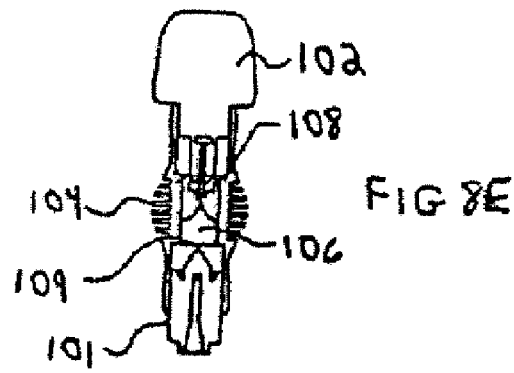
FIG. 8E is a sectional side elevation view corresponding to FIG. 8D.

As seen in FIGS. 8D and 8E, after capillary channel 105 has been filled with a blood sample, first portion 102 is then inserted into second portion 104 such that septum piercing projection 103 pierces through top septum 108, such that capillary channel 105 is received into treatment solution chamber 106. Thus, the contents of capillary channel 105 and treatment solution chamber 106 mix together. Mixing may be further enhanced by shaking the device.

Figure 8F:
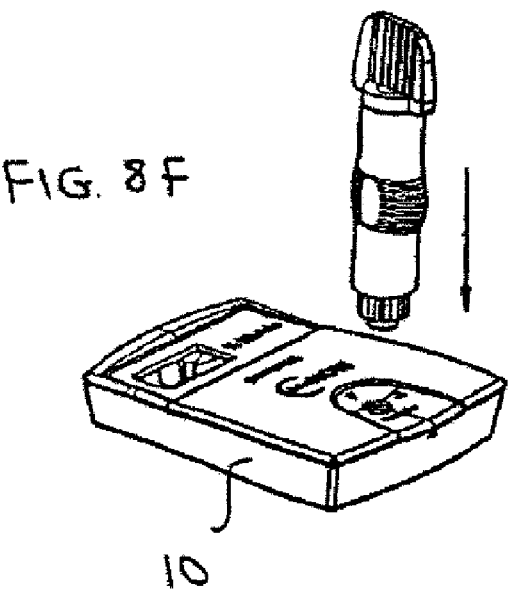
FIG. 8F is a perspective view of the eighth embodiment of the invention being inserted into a meter.
Figure 8G:
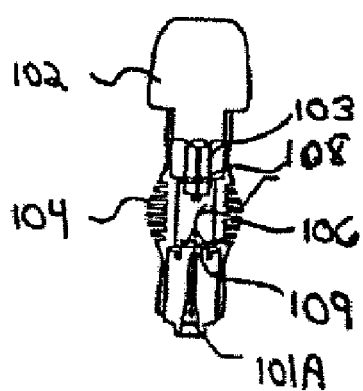
FIG. 8G is a sectional side elevation view corresponding to FIG. 8F.

Lastly, as seen in FIGS. 8F and 8G, dispensing nozzle 101 can be moved with respect to first portion 102 such that a second (i.e.: bottom) septum 109 is penetrated by first portion 102. When this occurs, the mixed blood/treatment solution is ejected from the device through dispensing nozzle 101. In preferred embodiments, distal end 101A of dispensing nozzle 101 is dimensioned to be received into a port of a blood analyte meter 10 (that may optionally comprise a hemoglobin A1c blood meter). It is to be understood, however, that this embodiment of the invention may also be used with any suitable fluid analysis meter, or even with a simple containment vessel (e.g.: for preparing a sample for deposition in a well, such that it can be analyzed in future).

Referring back to FIG. SC, optional internal features of dispensing nozzle 101 are illustrated. For example, (in contrast to FIG. 8C), the internal channel 120 through which fluid is ejected can be flared. This has the advantage of slowing the flow of solution into meter 10, which prevents splashing inside meter 10. In addition, an air vent 120 can also be provided to air pressure buildup during operation.

Also, in preferred embodiments, dispensing nozzle 101 is received into first portion 104, as illustrated. This has the advantage of trapping the blood/treatment solution mixture such that it can all be ejected through dispensing nozzle 101.

First and second septums 108 and 109 may be made of foil. However, the present invention is not so limited. Septums 108 and 109 may be made of any suitable material, including plastic or rubber.

System 100 may also be used for preparing a blood sample for use in a blood analyte meter 10 by: drawing blood into capillary channel 105 in a body 102 having a septum piercing projection 103; piercing a first septum 108 covering treatment solution chamber 106 with septum piercing projection 103, thereby exposing the blood in capillary channel 105 to the contents of treatment solution chamber 106; shaking treatment solution chamber 106 with capillary channel 105 received therein, thereby mixing the blood with the contents of treatment solution chamber 106; and piercing a second septum 109 such that the mixed blood and treatment solution chamber contents are received into blood analyte meter 10.

System 100 may also be used for preparing a blood sample for use in blood analyte meter 10, by: drawing a blood sample into capillary channel 105 in first portion 102 of the device; moving a first portion 102 of the device with respect to second portion 104 to penetrate septum 108 of treatment solution chamber 106 such that contents of treatment solution chamber 106 are mixed with the blood sample in capillary channel 105; and ejecting the mixed treatment solution and blood sample through dispensing nozzle 106 and into a blood analyte meter 10.

FIG. 8H illustrates a system for easier washout of capillary channel 105 in septum piercing projection 103 of first portion 102, as follows. An open window 109 is provided in the side of capillary channel 105 to permit easier washout of the fluid sample, such that the device can be re-used.

The invention claimed is:

1. A method of preparing a fluid sample for use in a fluid analyte monitor, comprising:

drawing a fluid sample into a capillary channel in a body having a septum piercing projection;

piercing a first septum covering a treatment solution chamber with the septum piercing projection, thereby exposing the fluid sample in the capillary channel to the contents of the treatment solution chamber;

shaking the treatment solution chamber with the capillary channel therein, thereby mixing the fluid sample with the contents of the treatment solution chamber; and piercing a second septum covering the treatment solution chamber such that the mixed fluid and treatment solution chamber contents are received into a fluid analyte meter.

2. The method of claim 1, wherein the fluid sample is blood.

3. The method of claim 1, wherein the fluid sample is interstitial fluid.

4. The method of claim 1, wherein the septum piercing projection and the capillary channel are disposed on a first portion of a device, and wherein the treatment solution chamber and the first septum covering the treatment solution chamber are disposed on a second portion of the device, and wherein the first and second portions of the device mate together.

5. The method of claim 1 wherein the septum piercing projection pierces through the first septum, such that the capillary channel is received into the treatment solution chamber when the first portion of the device is inserted into the second portion of the device.

6. The method of claim 1 wherein the second portion is dimensioned such that the second septum is pierced so as to release the contents of the treatment solution chamber into a fluid analyte meter, when the second portion of the device is received into a port in the fluid analyte meter.

7. A method of using a device to prepare a fluid sample for use in a fluid analyte meter, comprising:

drawing a fluid sample into a capillary channel in a first portion of the device, the first portion having a component adapted to penetrate a septum;

moving a second portion of the device comprising a treatment solution chamber with respect to the first portion of the device to penetrate a septum of the treatment solution chamber such that contents of the treatment solution chamber are mixed with the fluid sample in the capillary channel; and ejecting the mixed treatment solution and fluid sample through a dispensing nozzle of the first portion of the device and into a fluid analyte meter.

8. The method of claim 7, further comprising:
mixing the contents of the treatment solution chamber with the fluid in the capillary channel by shaking the first portion of the device.

9. The method of claim 7, further comprising:
mixing the contents of the treatment solution chamber with the fluid in the capillary channel in a mixing chamber in the first portion of the device.

10. The method of claim 7, wherein the fluid sample is blood.

11. The method of claim 7, wherein the fluid sample is interstitial fluid.

12. The method of claim 7, wherein the fluid sample contains prostate specific antigen.

13. A method of preparing a fluid sample for use in a fluid analyte monitor, comprising:
drawing a fluid sample into a capillary channel in a body having a septum piercing projection;
piercing a first septum covering a treatment solution chamber with the septum piercing projection, thereby exposing the fluid sample in the capillary channel to the contents of the treatment solution chamber;
mixing the fluid sample with the contents of the treatment solution chamber; and
piercing a second septum covering the treatment solution chamber such that the mixed fluid and treatment solution chamber contents are received into a fluid analyte meter.

14. The method of claim 13, wherein the fluid sample is blood.

15. The method of claim 13, wherein the fluid sample is interstitial fluid.

16. The method of claim 13, wherein the septum piercing projection and the capillary channel are disposed on a first portion of a device, and wherein the treatment solution chamber and the first septum covering the treatment solution chamber are disposed on a second portion of the device, and wherein the first and second portions of the device mate together.

17. The method of claim 13 wherein the septum piercing projection pierces through the first septum, such that the capillary channel is received into the treatment solution chamber when the first portion of the device is inserted into the second portion of the device.

18. The method of claim 13 wherein the second portion is dimensioned such that the second septum is pierced so as to release the contents of the treatment solution chamber into a fluid analyte meter, when the second portion of the device is received into a port in the fluid analyte meter.

19. The method of claim 14, wherein said mixing is achieved by shaking the treatment solution chamber with the capillary channel therein.

20. The method of claim 15, wherein said mixing is achieved by shaking the treatment solution chamber with the capillary channel therein.

* * * * *